(12) United States Patent
Harvey et al.

(10) Patent No.: US 12,152,003 B1
(45) Date of Patent: Nov. 26, 2024

(54) CHEMOSELECTIVE HYDROGENATION OF TERPENES WITH CYCLOPROPANE GROUPS

(71) Applicant: The United States of America, as represented by the Secretary of the Navy, Arlington, VA (US)

(72) Inventors: Benjamin G. Harvey, Ridgecrest, CA (US); Joseanne Dee Woodroffe, Ridgecrest, CA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 18/128,520

(22) Filed: Mar. 30, 2023

Related U.S. Application Data

(60) Provisional application No. 63/325,840, filed on Mar. 31, 2022.

(51) Int. Cl.
| | |
|---|---|
| *C07C 5/03* | (2006.01) |
| *B01J 23/44* | (2006.01) |
| *B01J 23/56* | (2006.01) |
| *C07C 5/10* | (2006.01) |
| *C07C 7/04* | (2006.01) |

(52) U.S. Cl.
CPC .............. *C07C 5/03* (2013.01); *B01J 23/44* (2013.01); *B01J 23/56* (2013.01); *C07C 5/10* (2013.01); *C07C 7/04* (2013.01)

(58) Field of Classification Search
CPC ..... C07C 5/03; C07C 5/10; C07C 7/04; B01J 23/44; B01J 23/56
See application file for complete search history.

(56) References Cited

U.S. PATENT DOCUMENTS 9,777,234 B1 * 10/2017 Harvey ................... C07C 5/13

FOREIGN PATENT DOCUMENTS

CN 104151126 B * 1/2016

OTHER PUBLICATIONS

Translation of CN104151126B (Year: 2016).*

* cited by examiner

*Primary Examiner* — Ali Z Fadhel
(74) *Attorney, Agent, or Firm* — Naval Air Warfare Center Weapons Division; Stuart H. Nissim

(57) ABSTRACT

The present invention provides a novel method for chemoselectively hydrogenating cyclic monoterpene precursors with reduced $PtO_2$ at low temperatures, to yield products in which the alkene groups are saturated while the cyclopropane rings from the parent hydrocarbons are conserved.

16 Claims, 3 Drawing Sheets tetrahydrosabinene (2)     sabinene     thujane (1)

1,1,4-trimethyl-cycloheptane (4)     3-carene     carane (3)

CHEMOSELECTIVE HYDROGENATION OF TERPENES WITH CYCLOPROPANE GROUPS

CROSS-REFERENCE TO RELATED APPLICATIONS

This application is a nonprovisional application claiming the benefit of U.S. provisional application No. 63/325,840, filed on Mar. 31, 2022, the contents of which are hereby expressly incorporated by reference in its entirety and which priority is claimed.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND OF THE INVENTION

There is an ever increasing need to find sustainable substitutes for petroleum-based products. Important areas of need for such products include sustainable polymers and sustainable aviation fuel (SAF). SAF can be produced from a number of renewable substrates including vegetable oils, lignocellulosic feedstocks, sewage, and even carbon dioxide. As these fuels are developed, a key consideration is that SAF must have properties that are comparable to or exceed those of conventional jet fuels. Cycloalkanes are an important component of jet fuels that impart high density and increased volumetric net heat of combustion (NHOC), while providing acceptable combustion properties and low temperature viscosities. In addition, recent research has suggested that cycloalkanes can potentially be used to replace aromatic compounds in SAF blends, improving gravimetric NHOC and reducing particulate emissions, while maintaining the essential seal-swelling properties exhibited by conventional jet fuel.

Conventional jet fuel has a density of ~0.8 g/mL, a gravimetric net heat of combustion (NHOC)≥ to 42.8 MJ/kg, and a volumetric NHOC≥ to 33.17 MJ/L. Increasing the gravimetric and/or volumetric NHOC of jet fuels can increase the range of aircraft or the amount of cargo that can be carried.

Terpenes are a class of molecules with applications for jet and rocket propulsion. Cyclic terpenes are naturally occurring cycloalkanes (primarily unsaturated) that can be obtained from plant extracts or produced via fermentation of biomass sugars with metabolically engineered organisms. Several terpenes, including sabinene and 3-carene, contain ring-strained (~114 kJ/mole) cyclopropane groups, which increase the density of the fuel while simultaneously maintaining a high gravimetric heat of combustion. Conventional hydrogenation of cyclopropanes results in ring-opening reactions, reducing the density of derivative fuels.

The current invention describes methods for the chemoselective hydrogenation of terpenes, in which alkenes are saturated without ring opening of the cyclopropane rings. Purification of the hydrogenation products then results in the isolation of high-performance jet fuel blendstocks exhibiting higher gravimetric and volumetric heats of combustion compared to conventional jet fuels, while imparting low viscosities and freezing points.

DEFINITIONS

Figure 1:
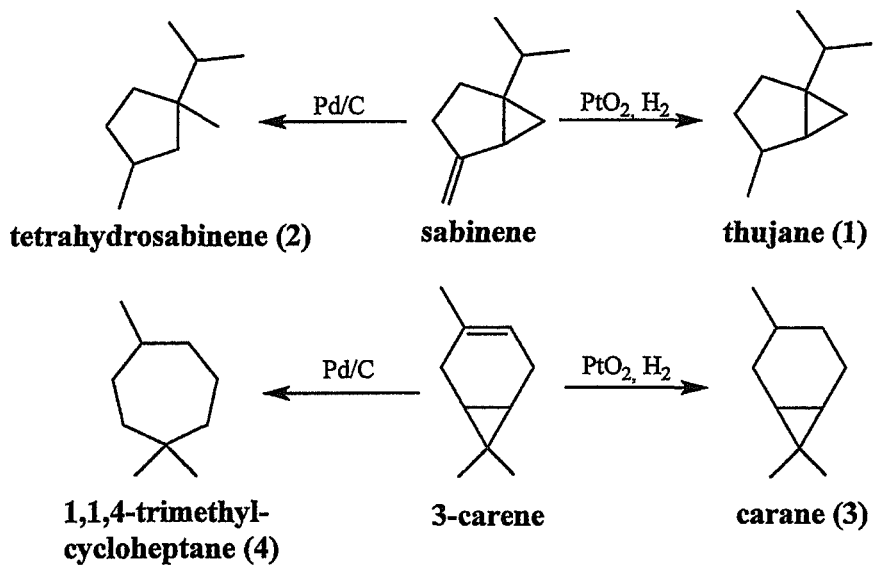
FIG. 1 is an illustration of synthetic pathways for chemoselective hydrogenation, according to embodiments of the invention.
Figure 2:
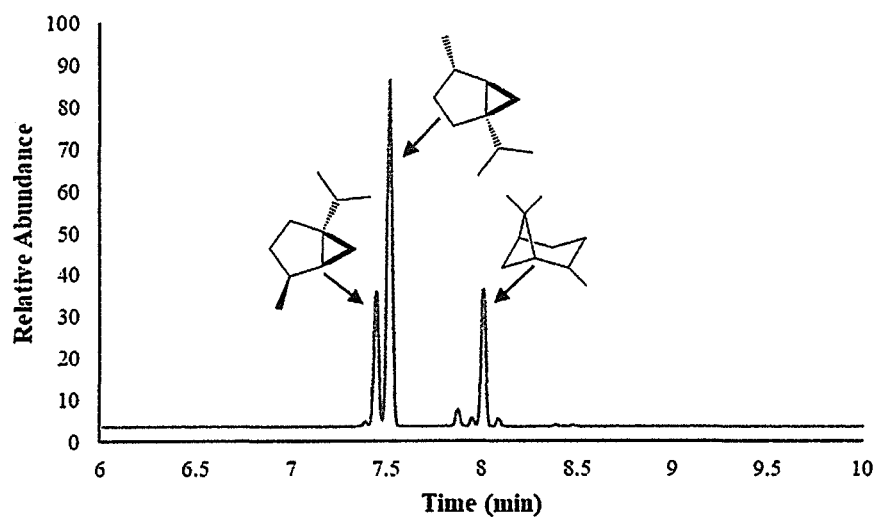
FIG. 2 is a gas chromatogram of a hydrogenated sabinene/p-pinene mixture, according to embodiments of the invention.
Figure 3:
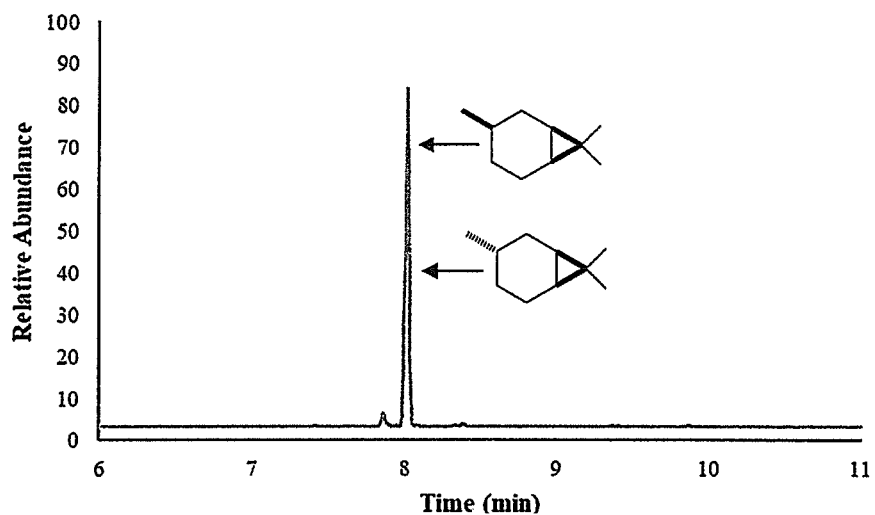
FIG. 3 is a gas chromatogram of hydrogenated cis- and trans-carane, according to embodiments of the invention.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Reference throughout the specification to "one example", "another example", "an example", and so forth, means that a particular element (e.g., feature, structure, and/or characteristic) described in connection with the example is included in at least one example described below, and may or may not be present in other examples. In addition, it is to be understood that the described elements for any example may be combined in any suitable manner in the various examples unless the context clearly dictates otherwise.

In describing and claiming the examples described below, the singular forms "a", "an", and "the" include plural referents unless the context clearly dictates otherwise.

As used herein, the terms "about" or "approximately" mean within an acceptable range for the particular parameter specified as determined by one of ordinary skill in the art, which will depend in part on how the value is measured or determined, e.g., the limitations of the sample preparation and measurement system. Example of such limitations include preparing the sample in wet versus a dry environment, different instruments, variations in sample height, and differing requirements in signal-to-noise ratios. The use of numerical values in the various ranges specified in this application, unless expressly indicated otherwise, are stated as approximations as though the minimum and maximum values within the stated ranges are both preceded by the word "about" or "approximately". In this manner, slight variations above and below the stated ranges can be used to achieve substantially the same results as values within the ranges. Also, unless indicated otherwise, the disclosure of these ranges is intended as a continuous range including every value between the minimum and maximum values.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

The definitions and understandings of cycloalkenes and fuels, are known to those of skill in the art, and such definitions are incorporated herein for the purposes of understanding the general nature of the subject matter of the present application. However, the following discussion is useful as a further understanding of some of these terms.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE EMBODIMENTS OF THE INVENTION

Embodiments of the invention generally relate to the facile, high yield synthesis of hydrogenated multicyclic sesquiterpencs (C15 hydrocarbons). Such hydrogenated multicyclic sesquiterpenes have been shown to be useful as high-density fuels for volume-limited applications, while hydrogenated cyclic monoterpenes (C10 hydrocarbons) have boiling points and viscosities suitable for high blend ratios with conventional jet fuels and other SAFs. In addition to cyclohexane and cyclopentane-based molecules similar to cyclic alkanes found in conventional jet fuel. The natural diversity of monoterpenes allows access to molecules with unique structures, including strained ting systems (e.g., cyclobutane or cyclopropane), which result in increased NHOCs and higher densities, allowing them to outperform Jet-A. Examples of promising fuels with small ring systems include cyclopropanated monoterpenes, alkyl cyclobutanes, and oligomeric cyclopropanes (ivyanes).

One embodiment of the method comprises:

A terpene containing a cyclopropane ring or a synthetic cycloalkene containing a cyclopropane ring is provided; then the terpene or synthetic cycloalkene is subjected to low-temperature hydrogenation (ambient or subambient) in the presence of a heterogeneous catalyst; then the hydrogenated terpene or cycloalkene is separated from the catalyst and purified to produce a jet fuel blendstock.

In a further embodiment, the terpene or cycloalkene hydrogenation reaction can be conducted at an intermediate temperature to produce a mixture of the ring-opened product and the product with the cyclopropane ring intact.

In another embodiment, the hydrogenated terpene or cycloalkene can be mixed with conventional jet fuel or other alternative jet fuels.

In embodiments, the terpene or cycloalkene containing a cyclopropane ring is provided, which can include monoterpenes (C10), sesquiterpenes (C15), diterpenes (C20) and heavier oligomers. Examples of monoterpenes include sabinene, thujene, 3-carene and 2-carene. An example of a sesquiterpene is thujopsene. The terpenes can be sourced from plant extracts, gum turpentine or crude sulfate turpentine. Alternatively, the terpenes can be produced via a fermentation route using metabolically engineered microorganisms. In embodiments, a mixture of terpenes can be provided which includes a cyclopropane-containing terpene. In other embodiments, blends of terpenes can be prepared based on desired fuel properties (e.g. density, viscosity, heat of combustion).

In examples, the terpene or terpene blend is chemoselectively hydrogenated. To reduce or eliminate ring opening of the cyclopropane ring, a platinum-based hydrogenation catalyst is utilized and the hydrogenation is conducted at low temperature to intermediate (about −80° C. to about 50° C.). To further reduce or eliminate ring opening of the cyclopropane ring, the reaction is conducted at low pressure. In embodiments, the pressure is between about 1-100 psi. In embodiments, the catalyst is a heterogeneous catalyst. Preferred catalysts include PtO2, Pt dispersed on an inorganic or polymer support, platinum nanoparticles, etc. ~0.0001 to 1 mol % of the catalyst is used. In embodiments, acetic acid or another carboxylic acid is added to enhance the rate and completeness of the reaction. In embodiments, the acetic acid is used as a co-solvent and is present in a 1:5 to 1:10 ratio of acetic acid:alkene.

Following the hydrogenation, the hydrogenated product is purified by filtration, washing, and distillation. In preferred embodiments, the distillation is conducted under reduced pressure. The fuel product derived from the low-temperature hydrogenation of an 80:20 mixture of sabinene:beta-pinene has a gravimetric NHOC of 43.36 MJ/kg, a volumetric NHOC of 35.90 MJ/L, a density of 0.828 g/mL, a −20 C kinematic viscosity of 3.45 mmA2/s, a −40 C kinematic viscosity of 6.12 mmA2/s, and a flash point of 37 degrees C. (See Tables 1 and 2). The fuel product derived from the low-temperature hydrogenation of 3-carene has a gravimetric NHOC of 43.19 MJ/kg, a volumetric NHOC of 36.38 MJ/L, a density of 0.842 g/mL, a −20 C kinematic viscosity of 3.64 mmA2/s, a −40 C kinematic viscosity of 6.84 mmA2/s, and a flash point of 44 degrees C. (See Tables 1 and 4).

In other embodiments, the hydrogenation reaction can be conducted at higher temperatures and pressures than described above. This produces a mixture of fully hydrogenated (ring-opened) products along with molecules in which the cyclopropane ring is intact. The fuel properties of fully hydrogenated sabinene/beta-pinene and 3-carene can be found in Tables 1, 3, and 5.

The cyclopropane containing hydrocarbons can be blended with conventional jet fuel or alternative fuels. In embodiments, the cyclopropane containing hydrocarbons can be used in place of aromatic compounds to enhance the seal-swelling capability of alternative fuels, while simultaneously enhancing the gravimetric heat of combustion.

Preferred embodiments include the hydrogenation of the monoterpenes, 3-carene and sabinene, for example. In addition to the benefits of utilizing a renewable source, the chemoselectivity of the present process results in the products of the present method having superior characteristics compared to those of previous methods.

3-Carene is a bicyclic terpene present as a significant component of essential oils derived from various *Pinus* species including, *Pinus roxburghii* and *Pinus sylvestris*. It features a cyclohexene ring system fused to a cyclopropane ring, which is decorated with geminal methyl groups. Sabinene is a bicyclic monoterpene typically isolated from the essential oils of plants including, holm oak, Norway spruce, and *Juniperus Sabina*. It contains a cyclopentane ring with an exocyclic double bond, which is fused to a cyclopropane ring.

Although significant quantities of 3-carene and sabinene are available commercially, production of them at a scale sufficient for use in jet or rocket fuel would require fermentation of these molecules with metabolically engineered organisms. Fermentations to produce sabinene have been widely studied and titers as high as 15.9 g/L have been obtained via a cell-free enzymatic approach.

As illustrated in FIG. 1, to produce optimized fuel blendstocks from 3-carene and sabinene, it would be ideal to conduct a chemoselective hydrogenation that would reduce the alkenes while leaving the cyclopropane rings intact. Hydrogenation of sabinene with Pd/C results in the isolation of tetrahydrosabinene (2), while the hydrogenation of sabinene with $PtO_2$ and $NaBH_4$ at low temperature (about −20° C.) resulted in chemoselective hydrogenation of the double bond, yielding thujane (1). Similarly, the hydrogenation of 3-carene with a Pt catalyst has yielded primarily cis-carane (3), while reaction with Pd-based catalysts resulted in conversion to 1,1,4-trimethylcycloheptane (4). The present invention comprises a method to control the hydrogenation of sabinene and 3-carene at larger scale by selecting catalysts and reaction conditions (e.g., temperature/pressure) to allow for chemoselective hydrogenation of these two bio-based substrates. After synthesizing and characterizing the reduced hydrocarbons, key fuel properties including, density, gravimetric/volumetric NHOC, kinematic viscosity, and flash point compare favorably to other bio-based cycloalkanes and conventional jet fuel, demonstrating the advantages of the cyclopropane-containing molecules produced by the present invention.

Although embodiments of the invention are described in considerable detail, including references to certain versions thereof, other versions are possible. Therefore, the spirit and scope of the appended claims should not be limited to the description of versions included herein.

EXAMPLES

The following examples are for illustration purposes only and not to be used to limit any of the embodiments.

Example 1

Referring to FIG. 1, the synthesis of hydrogenated monoterpenes from sabinene and 3-carene. Conditions: a) $PtO_2$ catalyst, acetic acid co-solvent, temperature (−10° C. for sabinene; 25° C. for 3-carene), pressure (100 psi for sabinene; 50 psi for 3-carene). b) Pd/C catalyst, acetic acid co-solvent, temperature (25° C. for sabinene; 150° C. for 3-carene), pressure (40 psi for sabinene; 500 psi for 3-carene).

Example 2

Synthesis of 1-isopropyl-4-methylbicyclo[3.1.0]hexane (1, thujane) through the low-temperature hydrogenation of sabinene Referring to FIG. 1, a Parr reactor was charged with $PtO_2$ (0.6 g, 2.6 mmol), glacial acetic acid (18 mL) and sabinene (60.0 g, 0.44 mol) and cooled to −10° C. The reaction vessel was charged with hydrogen 3 times via pump/pressurize cycles, and then pressurized to 100 psi and stirred for 4 hours. The reaction mixture was filtered through Celite using diethyl ether (350 mL), and the filtrate was then washed with DI water (3×80 mL), a 10% aqueous solution of $Na_2CO_3$ (3×80 mL) and brine (2×80 mL). The organic extracts were dried with $MgSO_4$ and concentrated under reduced pressure. The crude product was then distilled under reduced pressure (2 mmHg) at 25 −26° C. to yield 53.24 g (87.5% yield) of a mixture of cis-thujane and trans-thujane diastereomers (78% of the GC-FID area) and pinane diastereomers (21% of the GC-FID area). 1H NMR (500 MHz, $CDCl_3$) δ 2.59-2.31 (m), 2.14-1.77 (m), 1.72-1.56 (m), 1.50-1.32 (m) 1.22-1.17 (m), 1.05-0.83 (m), 0.79-0.76 (m), 0.34-0.30 (m), 0.25-0.22 (m), 0.11-0.09 (m). 13C NMR of the major diastereomer, cis-thujane (125 MHz, $CDCl_3$) δ 34.39, 32.73, 29.89, 28.60, 24.53, 21.47, 20.42, 20.00, 19.76, 12.90. MS data for cis-thujane: 138, 123, 109, 95 m/z. Anal. Calcd for $C_{10}H_{18}$: C, 86.81; H, 13.11. Found: C, 85.07; H, 12.79.

Example 3

Complete Hydrogenation of Sabinene (Ring Opening)

10% Pd/C (0.5 g) and glacial acetic acid (10 mL) were added to sabinene (51.62 g, 0.38 mol). The reaction vessel was charged with hydrogen 3 times via pump/pressurize cycles, and then pressurized to 40 psi and shaken for 24 hours at ambient temperature. The workup was conducted as described in Example 2 for the low-temperature hydrogenation of sabinene.

The crude product was then purified by vacuum distillation (25-29° e, 1.6 mm.Hg) to yield 39.88 g (75.3% yield) of a mixture of tetrahydrosabinene diastereomers (81% of the Ge-FID area) and pinane diastereomers (19% of the Ge-FID area). 1H NMR (500 MHz, eDeb) δ 2.39-2.34 (m), 2.23-1.66 (m), 1.59-1.12 (m), 1.07-0.96 (m), 0.91-0.86 (m). 13e NMR for the tetrahydrosabinene isomers (125 MHz, eDeb) 848.7, 47.4, 46.2, 45.6, 39.5, 39.0, 38.6, 37.9, 35.1, 34.9, 34.0, 33.4, 23.8, 21.6, 21.3, 18.83, 18.79, 18.7, 18.3. MS data for the tetrahydrosabinene isomers: 140, 125, 97 m/z. Anal. calcd. for e10H19.53: e, 85.92; H, 14.08. Found: e, 86.11; H, 14.08.

Example 4

Synthesis of 1-isopropyl-4-methylbicyclo[3.1.0]hexane (1, thujane) at ambient temperature As described in Example 2, a Parr reactor was charged with $PtO_2$ (0.21 g, 0.94 mmol), glacial acetic acid (4 mL) and sabinene (16.09 g, 0.12 mol). The reactor was pressurized to 50 psi $H_2$, and stirred for 4 h at 17-19° C. The reaction mixture was filtered through Celite using diethyl ether (100 mL), and the filtrate was then washed with DI water (3×20 mL), a 10% aqueous solution of $Na_2CO_3$ (3×20 mL) and brine (2×20 mL). The organic extracts were dried with $MgSO_4$ and concentrated under reduced pressure to yield the crude product (89.9% yield) of a mixture of trans-thujane and cis-thujane diastereomers (75%), pinane diastereomers (23%), and tetrahydrosabinene (2%). The NMR and GC-MS data were consistent with the results described in Example 1.

Example 4

Synthesis of 1-isopropyl-1,3-dimethylcyclopentane (tetrahydrosabinene, 2)

Referring to FIG. 1, tetrahydrosabinene (2) was synthesized from sabinene with a 10% Pd/C catalyst in the presence of glacial acetic acid under 50 psi H$_2$ as described in the previous examples. The product was 76% tetrahydrosabinene diastereomers and 23% pinane diastereomers.

Example 5

Synthesis of 3,7,7-trimethylbicyclo[4.1.0]heptane (carane, 3) through an ambient-temperature hydrogenation of 3-carene Referring to FIG. 1, PtO$_2$ (0.55 g, 2.4 mmol) and glacial acetic acid (1 mL) were added to 3-carene (48.1 g, 0.35 mol) in a glass bomb. The reaction vessel was charged with hydrogen 3 times via pump/pressurize cycles, pressurized to 40 psi, and then shaken for 24 hours at ambient temperature. The reaction mixture was filtered through Celite with diethyl ether (250 mL), and the filtrate was then washed with a 10% aqueous solution of Na$_2$CO$_3$ (3×60 mL) and brine (2×60 mL). The organic extracts were dried with MgSO$_4$ and concentrated under reduced pressure. The crude product was then distilled under reduced pressure (25 mm Hg) at 85-86° C. to yield 45.86 g (89.4%) of a 72:28 mixture of cis:trans-carane diastereomers (97%) and 1,1,4-trimethylcycloheptane (3%). $^1$H NMR (500 MHz, CDCl$_3$) δ 2.00-1.71 (m), 1.49-1.38 (m), 1.33-1.26 (m), 1.23-1.12 (m), 1.05-1.03 (m), 1.00 (s), 0.96 (s), 0.93-0.89 (m), 0.87-0.86 (d), 0.85-0.83 (d), 0.82-0.61 (m), 0.56-0.52 (m), 0.45-0.41 (m). $^{13}$C NMR of the major diastereomer, cis-carane (125 MHz, CDCl$_3$) δ 31.18, 29.38, 28.69, 28.43, 22.19, 20.96, 19.83, 18.09, 15.46, 15.42. $^{13}$C NMR of the minor diastereomer, trans-carane (125 MHz, CDCl$_3$) δ. 31.00, 29.46, 28.36, 27.99, 22.86, 19.67, 19.43, 19.02, 17.35, 17.31. MS data for the carane diastereomers: 138, 123,109, 95m/z. Anal. Calcd for C$_{10}$H$_{18}$: C, 86.81; H, 13.11 Found: C, 85.70; H, 13.05.

Example 6

Synthesis of 1,1,4-trimethylcycloheptane (4) through the complete hydrogenation of 3-carene (ring opening)

Figure 4:
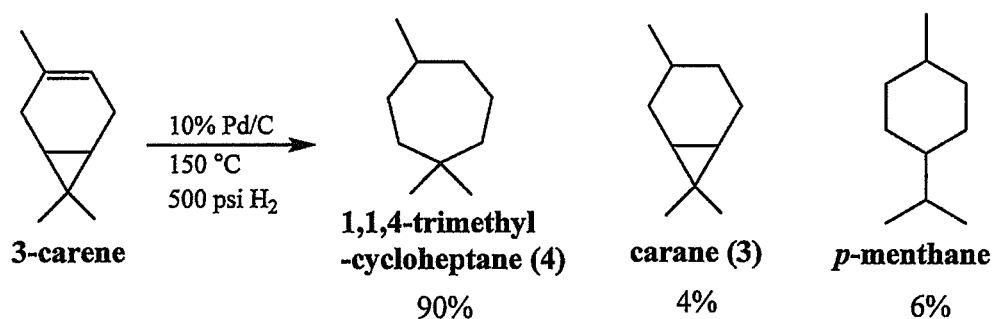
FIG. 4 is an illustration of synthetic pathways for the hydrogenation of 3-carene, according to embodiments of the invention.
Figure 5:
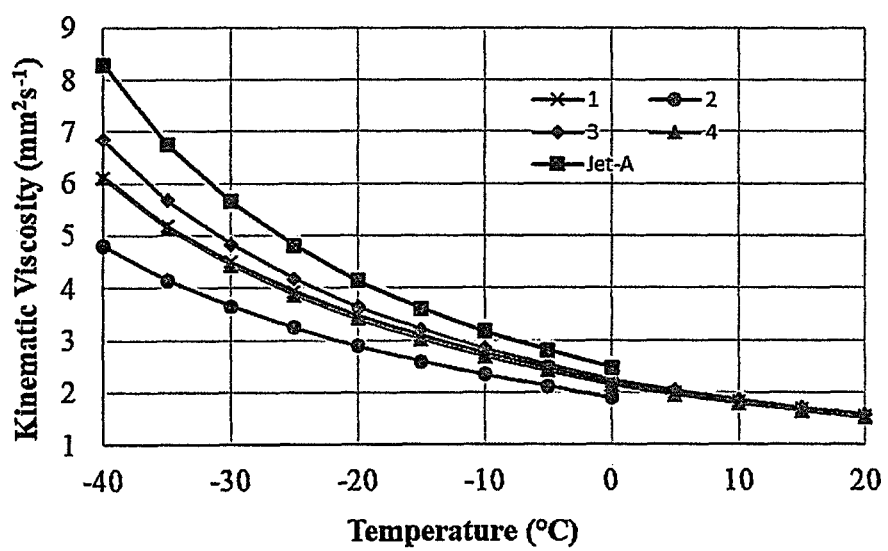
FIG. 5 is a graph showing kinematic viscosity of blendstocks 1-4 and Jet-A, according to embodiments of the invention.

Referring to FIG. 4, a Parr reactor was charged with Pd/C (0.2 g), glacial acetic acid (2 mL) and 3-carene (12.57 g, 0.092 mol). The reaction vessel was charged with hydrogen 3 times via pump/pressurize cycles, pressurized to 500 psi, and then stirred for 24 h at 150° C. The reaction mixture was filtered through Celite using diethyl ether (50 mL), and the filtrate was then washed with a 10% aqueous solution of Na$_2$CO$_3$ (3×10 mL) and brine (2×10 mL). The organic extracts were dried with MgSO$_4$ and concentrated under reduced pressure. The crude product was then distilled under reduced pressure (22.6 mm Hg) at 56-59° C. to yield 12.75 g (83.42%) of 4 (90% of the GC-FID area). 1H NMR (500 MHz, CDCl3) δ. 1.82-1.76 (m), 1.55-1.14 (m), 1.05-0.82 (in). 13C NMR for 4 (125 MHz, CDCl3) δ 42.28, 40.26, 39.73, 36.70, 33.22, 31.54, 31.03, 30.46, 23.90, 22.16. MS data for 4:140, 125, 97 m/z. Anal. Calcd for C10H20: C, 85.63; H, 14.37. Found: C, 85.52; H, 14.38.

TABLE 1

Key fuel properties of hydrogenated fuels.

| Fuel | NHOC (MJ kg$^{-1}$) | NHOC (MJ L$^{-1}$) | ρ 15° C., g mL$^{-1}$ | η −20° C., mm$^2$ s$^{-1}$ | η −40° C., mm$^2$ s$^{-1}$ | FP (° C.) |
|---|---|---|---|---|---|---|
| Jet A-1 | >42.80 | >33.17 | >0.775 | <8.0 | — | — |
| Thujane | 43.363 | 35.90 | 0.828 | 3.47 | 6.12 | 37 |
| Tetrahydrosabinene | 43.25 | 35.05 | 0.810 | 2.89 | 4.809 | 39 |
| Dihydro-3-carene | 43.19 | 36.38 | 0.842 | 3.64 | 6.835 | 44 |
| 1,1,4-Trimethyl cycloheptane | 43.02 | 34.69 | 0.806 | 3.40 | 6.109 | 42 |

TABLE 2

Kinematic viscosity and density of thujane.

| Cell Temp (° C.) | Kinematic Viscosity (mm$^2$/s) | Density (g/mL) |
|---|---|---|
| 20.00 | 1.5586 | 0.82369 |
| 15.00 | 1.6861 | 0.82794 |
| 10.00 | 1.8335 | 0.83199 |
| 5.00 | 2.0039 | 0.83599 |
| 0.00 | 2.2008 | 0.83995 |
| −5.00 | 2.4767 | 0.84374 |
| −10.00 | 2.7579 | 0.84764 |
| −15.00 | 3.0866 | 0.85154 |
| −20.00 | 3.4753 | 0.85544 |
| −25.00 | 3.9398 | 0.85934 |
| −30.00 | 4.5001 | 0.86323 |
| −35.00 | 5.1883 | 0.86710 |
| −40.00 | 6.1155 | 0.87092 |

TABLE 3

Kinematic viscosity and density of the tetrahydrosabinene/pinane blend.

| Cell Temp (° C.) | Kin. Viscosity (mm$^2$/s) | Density (g/mL) |
|---|---|---|
| 0.000 | 1.901 | 0.8226 |
| −5.000 | 2.124 | 0.8264 |
| −10.000 | 2.343 | 0.8302 |
| −15.000 | 2.596 | 0.8340 |
| −20.001 | 2.892 | 0.8377 |
| −25.001 | 3.241 | 0.8415 |
| −30.001 | 3.654 | 0.8452 |
| −35.001 | 4.149 | 0.8489 |
| −40.000 | 4.804 | 0.8526 |

TABLE 4

Kinematic viscosity and density of dihydro-3-carene.

| Cell Temp (° C.) | Kinematic Viscosity (mm$^2$/s) | Density (g/mL) |
|---|---|---|
| 20.00 | 1.5724 | 0.83832 |
| 15.00 | 1.7033 | 0.84246 |
| 10.00 | 1.8568 | 0.84643 |
| 5.00 | 2.0356 | 0.85036 |
| 0.00 | 2.2462 | 0.85424 |
| −5.00 | 2.5372 | 0.85800 |
| −10.00 | 2.8423 | 0.86184 |
| −15.00 | 3.2055 | 0.86569 |
| −20.00 | 3.6428 | 0.86954 |
| −25.00 | 4.1777 | 0.87338 |
| −30.00 | 4.8387 | 0.87723 |
| −35.00 | 5.6771 | 0.88104 |
| −40.00 | 6.8354 | 0.88466 |

TABLE 5

Kinematic viscosity and density of 1,1,2-trimethyl cycloheptane

| Cell Temp (° C.) | Kinematic Viscosity (mm$^2$/s) | Density (g/mL) |
|---|---|---|
| 20.00 | 1.5222 | 0.80242 |
| 15.00 | 1.6467 | 0.80636 |
| 10.00 | 1.7874 | 0.81012 |
| 5.00 | 1.9519 | 0.81386 |
| 0.00 | 2.1407 | 0.81761 |
| −5.00 | 2.4120 | 0.82117 |
| −10.00 | 2.6893 | 0.82486 |
| −15.00 | 3.0152 | 0.82858 |
| −20.00 | 3.4042 | 0.83229 |
| −25.00 | 3.8710 | 0.83602 |
| −30.00 | 4.4424 | 0.83975 |
| −35.00 | 5.1507 | 0.84349 |
| −40.00 | 6.1087 | 0.84718 |

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

The invention claimed is:

1. A method for the chemoselective hydrogenation of cycloalkene, comprising
    obtaining a cycloalkene having at least one alkene group and at least one cyclopropane group; and,
    hydrogenating the cycloalkene with a catalyst;
    controlling the degree of hydrogenation through temperature;
    wherein the at least one alkene group is saturated and the at least one cyclopropane group is conserved.

2. The method of claim 1, further comprising purifying the hydrogenated cycloalkene by filtration, washing, and distillation.

3. The method of claim 1, wherein the cycloalkene is a monoterpene (C10), a sesquiterpene (C15), a diterpene (C20), a heavier oligomer, or combinations thereof.

4. The method of claim 3, wherein the cycloalkene is sabinene, thujene, 3-carene, 2-carene, thujopsene, or combinations thereof.

5. The method of claim 1 wherein controlling the degree of hydrogenation further comprises catalyst selection.

6. The method of claim 5, wherein the catalyst is a heterogenous catalyst.

7. The method of claim 5, wherein the catalyst is a platinum-based hydrogenation catalyst.

8. The method of claim 5, wherein the catalyst is a Pd-based hydrogenation catalyst.

9. The method of claim 5, wherein the catalyst is about 0.0001 to about 1 mol %.

10. The method of claim 1, wherein the hydrogenation is conducted at or below ambient temperature.

11. The method of claim 1, wherein the hydrogenation is conducted at between about −80° C. to about 50° C.

12. The method of claim 1, wherein the hydrogenation is conducted at low pressure between about 1 to about 100 psi.

13. The method of claim 1 wherein a carboxylic acid is added as a co-solvent.

14. The method of claim 13 wherein the carboxylic acid as added in about a 1:5 to about a 1:10 ratio of carboxylic acid:cycloalkane.

15. The method of claim 13 wherein the carboxylic acid is acetic acid.

16. A fuel blend comprising jet fuel and the hydrogenated cycloalkene produced by the method of claim 1.

* * * * *